(12) United States Patent
Pressler et al.

(10) Patent No.: US 8,246,666 B2
(45) Date of Patent: Aug. 21, 2012

(54) PHOTOTHERAPY GARMENT

(75) Inventors: Tiffany J. Pressler, Conway, AR (US); Robert E. McGehee, Jr., Little Rock, AR (US); Jeffrey R. Kaiser, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 492 days.

(21) Appl. No.: 12/590,188

(22) Filed: Nov. 4, 2009

(65) Prior Publication Data

US 2010/0114263 A1  May 6, 2010

Related U.S. Application Data

(60) Provisional application No. 61/198,191, filed on Nov. 4, 2008.

(51) Int. Cl.
*A61N 5/06* (2006.01)
(52) U.S. Cl. .................... 607/88; 606/9; 606/2
(58) Field of Classification Search .............. 607/88; 606/9, 2
See application file for complete search history.

(56) References Cited

U.S. PATENT DOCUMENTS 5,698,866 A     12/1997  Doiron et al.
6,045,575 A *    4/2000  Rosen et al. .............. 607/88
6,596,016 B1 *   7/2003  Vreman et al. ............ 607/88

OTHER PUBLICATIONS

Porter, M., et al., Hyperbilirubinemia in the Term Newborn, American Family Physician, vol. 65, No. 4, pp. 599-606, Feb. 15, 2002.
Maisels, M., et al., Phototherapy for Neonatal Jaundice, New England Journal of Medicine, 358: 920-8, Feb. 28, 2008.
Management of Hyperbilirubinemia in the Newborn Infant 35 or More Weeks of Gestation, Pediatrics, vol. 114, No. 1, pp. 297-316, Jul. 2004.
GE Healthcare Launches Lullaby(TM) Phototherapy System in India for Infant Jaundice Treatment, http://www.ge.com/in/news/20071112.html, Nov. 12, 2007.
Suresh, G., et al., Cost-Effectiveness Strategies That are Intended to Prevent Kernicterus in Newborn Infants, Pediatrics, vol. 114, No. 4, pp. 917-924, Oct. 2004.
Rogowski, J., Measuring the Cost of Natal and Perinatal Care, Pediatrics, vol. 103, No. 1, pp. 329-335, Jan. 1999.

(Continued)

Primary Examiner — Kinam Park
(74) Attorney, Agent, or Firm — Ray F. Cox, Jr.

(57) ABSTRACT

A phototherapy garment including a form-fitting bodysuit having a shell made from a stretchable, washable material covering the arms, legs, and torso which provides phototherapeutic light via a layer of cross-woven side-glow optical fibers. The bodysuit has an adjustable fastening system along the arms, legs, and torso to allow for variable sizing and a snug fit. Light is transmitted into the fibers via a waterproof base unit that is detachably attached to a housing dock on the side of the bodysuit. The LEDs emit high-intensity light of a wavelength or wavelengths suitable for treatment of various medical conditions. Each wavelength is transmitted separately into a respective one of a series of cross-woven optical fibers. Optionally, a reflective liner within the bodysuit may redirect irradiation from the fibers back toward the skin so no energy is wasted. Another embodiment includes a transparent liner. The base unit includes a power supply that may includes a rechargeable battery. The suit may also include biofeedback and data logging systems.

14 Claims, 5 Drawing Sheets

OTHER PUBLICATIONS

Maternity Management Program Overview, http://www.alere.com/wchealth/resources/program-overviews/maternalink-maternity-management, Inverness Medical, 2 pages, 2009.

Paul, I., et al., Cost-Effectiveness of Postnatal Home Nursing Visits for Prevention of Hospital Care for Jaundice and Dehydration, Pediatrics, 114: 1015-1022, Oct. 2004.

Bilibee LED Phototherapy Treatment Equipment for Neonatal Jaundice, http://www.medicalselect.net/Overview/, Medical Select, Inc., 14 pages, 2009.

BiliTX(TM) Phototherapy System, Philips Children's Medical Ventures, http://bilitx.respironics.com/lightsource.asp, 12 pages, 2009.

BiliBed® Phototherapy System, Medela AG, http://www.medela.com/ISBD/neonatology/bilibed/index.php, 6 pages, 2008.

BiliSoft (TM) LED Phototherapy System, GE Healthcare, http://www.instrumentarium.com/euen/maternal-infant-care/docs/BiliSoft_bro_e.pdf, 8 pages, 2007.

Biliblanket® Plus High Output Phototherapy System, GE Healthcare, http://www.gehealthcare.com/usen/perinatal/phototherapy/products/biliblanketpls.html, 2 pages, 2009.

neoBlue® LED Phototherapy, Natus Medical Incorporated, http://www.natus.com/index.cfm?page=products_1&crid=36&contentid=88, 8 pages, date unknown.

501(k) Summary, Bilibee LED® Phototherapy System, Food and Drug Administration, http://www.fda.gov/cdrh/pdf7/K072097.pdf, 5 pages, Oct. 2007.

* cited by examiner

PHOTOTHERAPY GARMENT

CROSS-REFERENCE TO RELATED APPLICATIONS

This application claims the benefit of U.S. Provisional Patent Application No. 61/198,191 filed Nov. 4, 2008, the disclosure of which is incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention relates to a garment that provides phototherapy, and in particular, to such a garment that provides treatment of hyperbilirubinemia in infants.

2. Brief Description of the Related Art

Current treatment using phototherapy for reduction of bilirubin includes two basic approaches. Current techniques involve either the placement of an infant in an isolette tank with directed use of high-powered fluorescent lighting, identified herein as "Method 1" or through posterior contact with an optical fiber, identified herein as "Method 2."

Method 1 can only be provided while the patient is in a hospital setting, a situation which significantly increases the cost of treatment. The patient is typically left naked or in a diaper only. Because the high-powered lighting produces heat, the infant's body temperature and hydration are closely monitored. As the intense light may damage the infant's eyes, they are covered with eye patches, a requirement that may lead to conjunctivitis. Furthermore, recent studies have shown that exposure of an infant's head to the intense light seen in phototherapy could contribute to a condition known as hypocalcemia.

Method 2 treatment, providing light in an optical fiber pad, reduces or removes some of the disadvantages of Method 1. Because the treatment is provided through optical fiber, there is decreased potential for dehydration and raised body temperature. Treatment can also be provided at home rather than in a hospital setting. However, Method 2 carries its own disadvantages. The optical fiber pad provides treatment to a limited surface area, potentially prolonging or limiting treatment. As the light propagates from the pad in all directions, half the irradiance produced by the pad is wasted and, depending on how the infant is wrapped, its eyes could still be affected by escaped irradiation from the fiber. The unit is connected through a thick connector cord to a power unit which provides light to the pad with a high-powered fluorescent or halogen light. Due to the high heat produced by this lighting system, a fan must operate within the unit continually or risk overheating of the unit and a potential fire hazard. As a result of this design, mobility is extremely limited.

U.S. Pat. No. 6,596,016 to Vreman et al. issued Jul. 22, 2003 addresses some of these concerns. Vreman discloses a phototherapy garment having an LED liner within the garment. Vreman discloses electronic circuitry inside the garment, close to the infant's skin which could be exposed to moisture. The design of the Vreman device allows for the light panel array to be put into a garment. However, based upon available information within the patent, the garment may not necessarily be washable and may render regular clothing unusable after treatment has commenced.

The limitations of the prior art are overcome by the present invention as described below.

BRIEF SUMMARY OF THE INVENTION

The phototherapy garment of the present invention comprises a form-fitting bodysuit, having a shell made from a stretchable, washable material covering the arms, legs, and torso which provides phototherapeutic light via a layer of cross-woven side-glow optical fibers. The bodysuit preferably has an adjustable fastening system along the arms, legs, and torso to allow for variable sizing and a snug fit. The bodysuit may have open areas, for example in the armpit or groin areas, for ventilation. Light is transmitted into the optical fiber layer via a self-contained waterproof base unit that clips into an attached housing dock on the side of the bodysuit. The base unit contains LEDs with lenses that couple the light output of the LEDs to respective ports that transmit light to respective optical fibers. In one embodiment, the base unit contains three high output LEDs transmitting wavelengths of 450 nm (violet light), 480 nm (blue), and 510 nm (green). Each wavelength is transmitted separately into a one of a series of optical fibers in the cross-woven layer disposed within the shell. The optical fibers may be acrylic fiber. The intensities of light emitted by each of the LEDs are selected with regard to the characteristics of the optical fibers in the optical fiber layer so as to provide a therapeutically effective level of light to the skin of the patient. In one embodiment, a reflective liner within the shell of the bodysuit redirects radiation from the optical fibers back toward the skin so that no energy is wasted. The base unit includes a power supply that includes the circuitry needed to drive the LEDs and preferably includes a rechargeable battery. Biofeedback and data logging systems may be included in some embodiments. Although in the preferred embodiment the base unit is portable, in some applications the base unit may be supplied with power from a wall outlet. Furthermore in portable applications, the battery or batteries in the power supply may be single use types as opposed to rechargeable. The cross-woven layer of optical fibers may be separated from the skin of the patient by a transparent or translucent layer of material.

This invention is an improvement of the phototherapy process used to treat hyperbilirubinemia in newborn infants. Current methods of phototherapy treatment are provided either by placement of an infant in an incubator tank with directed use of high-powered fluorescent lighting or through posterior contact with a fiber optic pad. Both of the current methods of phototherapy have disadvantages. Side effects documented from current treatments include: increased body temperature, dehydration, conjunctivitis and hypocalcemia.

The present invention has been carefully designed to mitigate these side effects. Specifically, with regard to Method 1, the present invention provides therapeutic irradiance through a fiber optic system that does not transmit heat. Side effects that currently cause serious concern and monitoring such as increased body temperature and subsequent dehydration are not a factor with the present invention. Similarly, because the light is contained within the bodysuit and directed only to the arms, legs, and torso, dangers to the eyes and exposure of light to the head are avoided. The present invention is preferably cordless and portable, allowing for proper treatment in transit, at home or in any location.

Likewise, the present invention utilizes the safety of a fiber optic design, but eliminates the mobility and safety concerns noted with Method 2 treatments. Therapeutic light is always in direct contact with the skin and is completely contained within the bodysuit shell. A reflective lining redirects irradiance toward the skin so no energy is wasted. The system is cordless and portable allowing for continuous, uninterrupted treatment at any location. The light system used to provide required irradiance is operated using high-output LEDs which do not produce heat, eliminating potential fire hazards or overheating of the unit or patient.

The device disclosed in Vreman patent indicates an electronic circuitry inside the garment, close to the infant's skin which could be exposed to moisture. The present invention avoids this possible safety hazard. The present invention contains no electronic circuitry within the element of the suit unit. All circuitry is contained within a durable, waterproof base unit. Furthermore, while irradiance with the present invention is provided through LEDs, actual propagation of the wavelengths is delivered through side-glow optical fibers. The design of the Vreman device allows for the light panel array to be put into a garment. However, based upon available information within the Vreman patent, the garment may not necessarily be washable and may render regular clothing unusable after treatment has commenced. The present invention preferably has a shell which is washable, inexpensive to manufacture, and may be discarded after treatment. It is designed to fit directly under regular clothing.

The expediency of treatment of hyperbilirubinemia is tied to three factors: the wavelength of light used (important because it determines the penetration of irradiance through the skin), the amount of surface area of the body that is treated, and the distance of the light source from the skin. The present invention optimizes all three factors while overcoming the limitations of the prior art.

The commercial applications of the present invention may be found in the fields of pediatrics, neonatalogy and dermatology. While the device is preferably designed to treat hyperbilirubinemia in newborn infants, the functionality of the device is not so limited and could be expanded to treat numerous other skin conditions, such as acne or eczema, using phototherapy treatment.

Various transcutaneous biofeedback sensors may be incorporated into the device so that the device could also be used to collect other data with infants or adults.

These and other features, objects and advantages of the present invention will become better understood from a consideration of the following detailed description of the preferred embodiments and appended claim in conjunction with the drawings as described following:

DETAILED DESCRIPTION OF THE INVENTION

With reference to FIGS. 1-5, the preferred embodiments of the present invention may be described.

Figure 1:
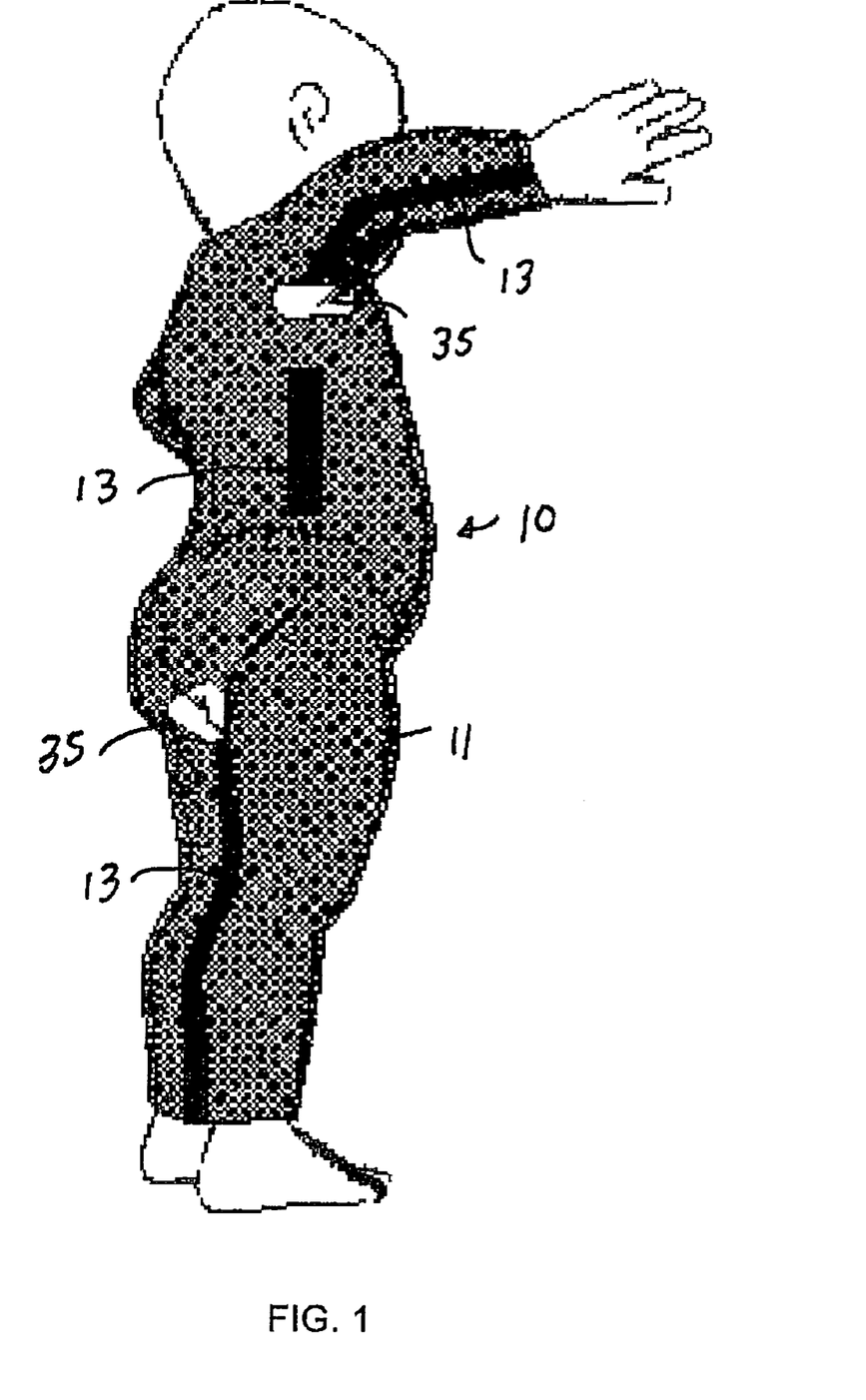
FIG. 1 is right side elevation view of a patient wearing the phototherapy garment of the present invention.
Figure 2:
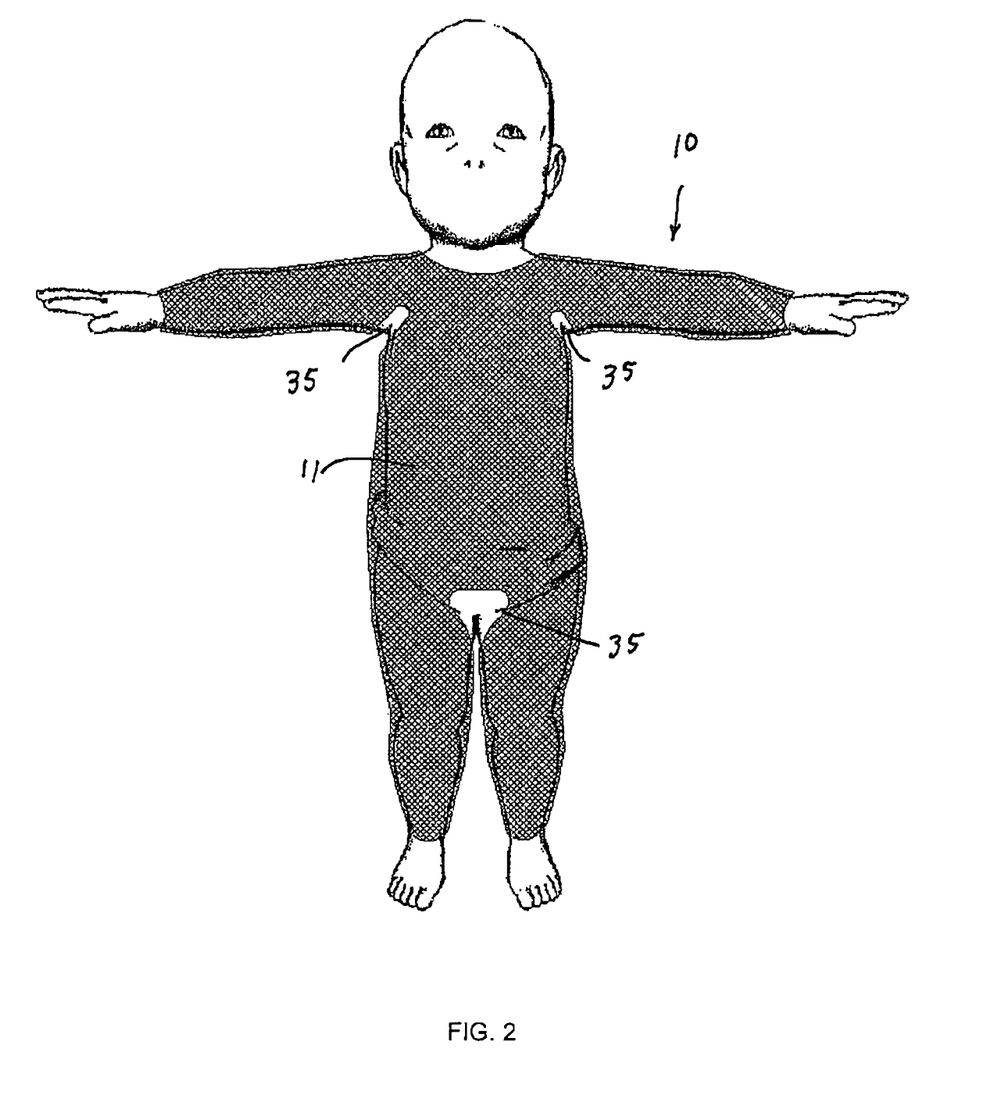
FIG. 2 is a front elevation view of a patient wearing the phototherapy garment of the present invention.
Figure 3:
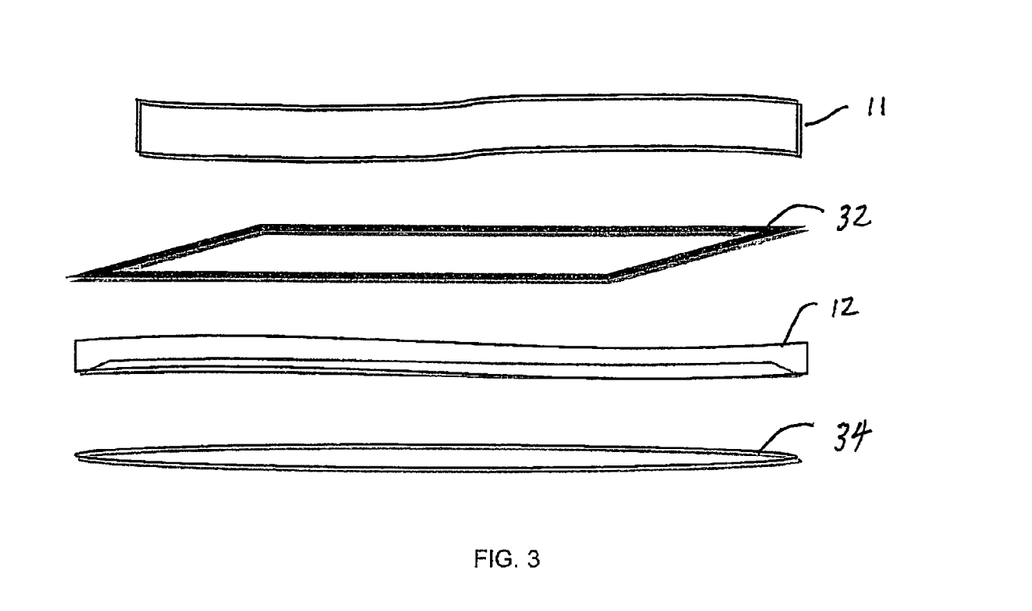
FIG. 3 is an exploded cross-sectional elevation view of the layers of an embodiment of the bodysuit of the present invention.
Figure 4:
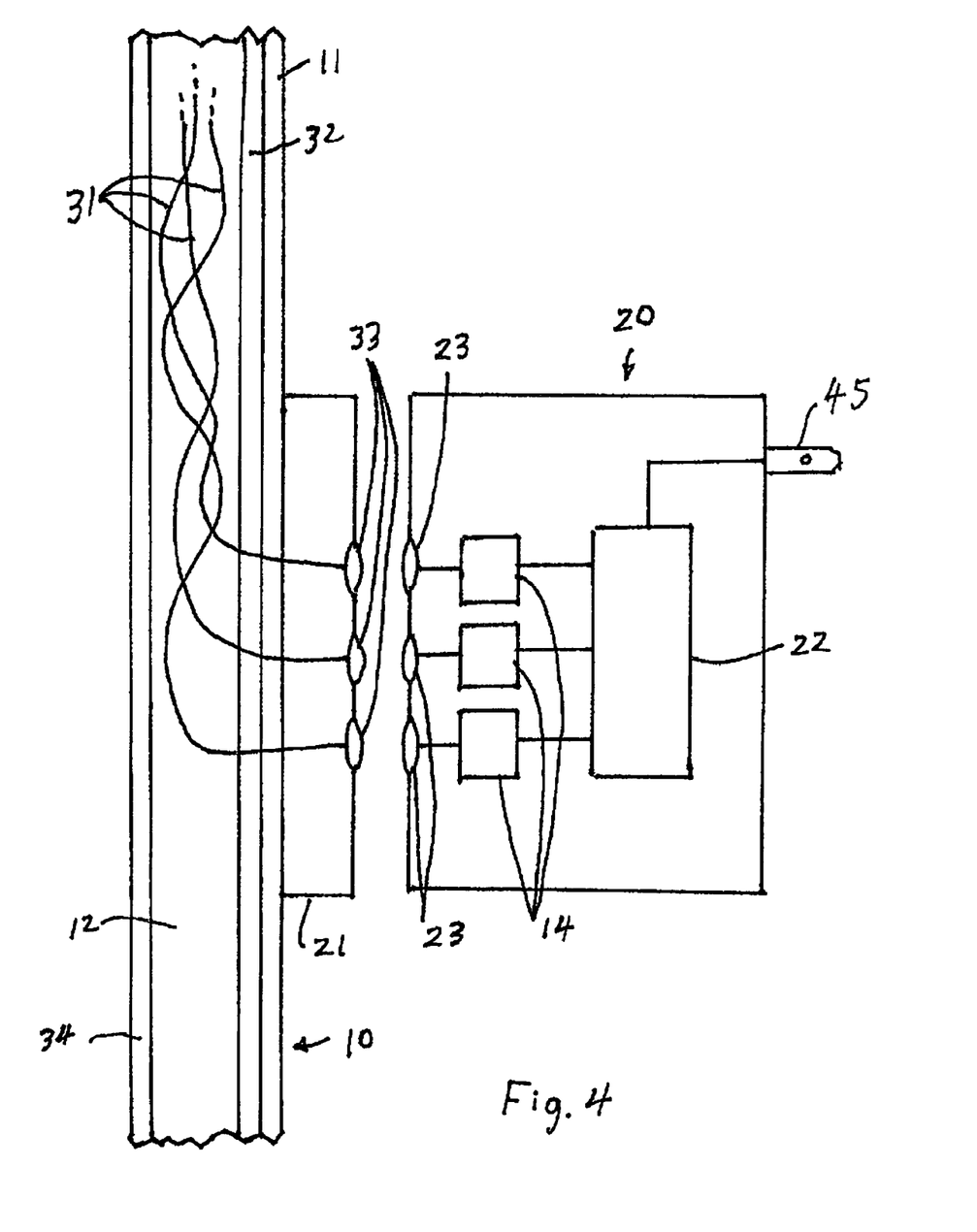
FIG. 4 is a schematic diagram of the base unit showing the connection of the base unit to the bodysuit through the housing dock on the bodysuit.

As shown in FIGS. 1 and 2, the present invention includes a form-fitting bodysuit 10 for phototherapy having a shell 11 made from a stretchable, washable material, such as polyester/spandex, covering the arms, legs, and torso of the patient. The bodysuit 10 may have open areas 35, for example in the armpit or groin areas, for ventilation. With reference to FIG. 3, a layer of cross-woven side-glow optical fibers 12 which provides phototherapeutic light is disposed within the shell 11 of the bodysuit 10. Acrylic optical fibers available from 3M are suitable for the practice of the present invention. As shown in FIG. 1, the bodysuit 10 has adjustable fasteners 13 along the arms, legs, and torso of the patient to allow for variable sizing and a snug fit. With reference to FIG. 4, light is transmitted into the layer of cross-woven optical fibers 12 from light emitting diodes ("LEDs") 14 contained within a waterproof base unit 20 that clips into an attached housing dock 21 on the side of the bodysuit 10. Each wavelength of light is transmitted separately into one of a series of cross-woven optical fibers 31. A reflective liner 32 within the bodysuit 10 redirects irradiation from the layer of cross-woven optical fibers 12 back toward the skin of the patient so that no energy is wasted.

The LEDs 14 emit high-intensity light of a wavelength or wavelengths suitable for treatment of various medical conditions. For example, the base unit 20 may contain three high output LEDs 14 transmitting wavelengths of 450 nm (violet light), 480 nm (blue), and 510 nm (green) optimized for the treatment of neonatal hyperbilirubinemia or Crigler-Najjar syndrome. An infant is placed inside the garment so that the LEDs 14 illuminate a large portion of the infant's skin for phototherapy.

In an alternative embodiment, a two-way communications device (not shown) may be incorporated into the garment to allow a physician or computer to control the garment remotely and gather relevant information periodically or continuously. The garment may also contain a feedback system (not shown) with, for example, skin bilirubin sensors, so that the intensity level and duration of light therapy for an infant with hyperbilirubinemia can be based on bilirubin in the skin, which is a reflection of a newborn's serum bilirubin concentration.

For treatment of an infant, it is desirable that the garment be lightweight and portable, allowing an infant to be treated at home, in the hospital, or when in transit. The garment provides high light intensity over a larger surface area of the newborn than allowed with existing techniques, thus providing very efficient phototherapy. The garment can be made into a form other than a bodysuit, but the bodysuit is preferred. Some types of garments are considered unsuitable for the treatment of certain conditions. For example, as described above, a hat or cap would be unsuitable for the treatment of hyperbilirubinemia in infants since some studies indicate that the exposure to high intensity light in the occipital region of the skull shows an increased incidence of hypocalcemia.

Bodysuit

In one embodiment, the present invention is designed to be unobtrusive, fitting snugly under regular clothing. The bodysuit 10 has adjustable fasteners 13 along the arms, legs, and torso to allow for one-size-fits-all manufacturing. The fastening system may, for example, use hook and loop type fasteners. The base unit 20 is detachably attached to the bodysuit 10 by means of a housing dock 21, making the bodysuit 10 with its attached housing dock 21 washable or disposable once treatment has been completed. The base unit 20 is reusable. Treatment is confined within the bodysuit 10 allowing for maximum coverage of surface area. Containment of irradiance within the bodysuit 10 is a key factor in eliminating potential side effects such as conjunctivitis, retinopathy, or hypocalcemia which may be found with current treatment methodologies. The overall design is intended to provide efficient, safe treatment without interference with child-parent bonding. Due to the bodysuit design, the patient is not confined to any particular location. Treatment may be provided continuously in transport, at home, or any other location.

Base Unit

The preferred embodiment of the base unit 20 is designed to be compact, portable, waterproof, and cordless. The base unit 20 snaps into and out of a housing dock 21 on the bodysuit 10 which allows reuse of the base unit 20 with multiple patients. The base unit 20 includes one or more LEDs 14 operatively connected to a power supply 22. The power supply 22 contains a power source and suitable circuitry to drive the LEDs 14. The housing dock 21 contains ports 33 which are optically connected to the optical fibers 31. When the base unit 20 is snapped into mechanical connection with the housing dock 21, lenses 23 associated with each of the LEDs 14 contained in the base unit 20 are optically aligned with the ports 33 in the housing dock 21 to transmit light from the LEDs 14 to the respective optical fibers 31. Preferably, the power supply 22 includes a rechargeable battery, such as a lithium ion battery, to allow the base unit 20 to be recharged between patient uses. The base unit 21 may be provided with an integral electric plug 45 for plugging into and recharging the rechargeable battery from a wall outlet. A roll-out type electrical plug suitable for this application is known in the art, for example, in camera batteries. In a preferred embodiment, three LEDs 14 provide optimized wavelengths intended to increase or improve incidence of configurational or structural isomerization of bilirubin in the blood. LEDs do not produce significant heat making them safe to use within the device.

Cross-Woven Optical Fiber Layer

Therapeutic irradiance is delivered to the skin of the patient through a layer of cross-woven side-glow optical fibers 12 including one or more optical fibers 31. The optical fibers 31 may be acrylic. As optical fibers do not transfer heat, required irradiance can be transmitted without raising body temperature and risking dehydration. An embodiment employing a single optical fiber 31 delivering one wavelength is within the scope of the present invention. Preferably, a plurality of optical fibers 31 are formed into a cross-woven layer disposed the shell 11 of the bodysuit 10 to allow constructive combination of their targeted wavelengths providing optimal efficacy. Because the wavelengths are combined in this fashion, favorable blue wavelengths can be used while avoiding "blue baby" syndrome.

Reflective Layer and Transparent Liner

In an alternative embodiment, a reflective layer 32 may be disposed between the outer shell 11 and the layer of cross-woven optical fibers 12. This design is intended to reuse or recycle irradiance so no intensity is wasted through misdirected light. In another alternative embodiment, a transparent liner 34 may be used between the layer of cross-woven optical fibers 12 and the skin of the patient.

Biofeedback and Data Logging Functionality

Readouts may be provided on demand or archived to a memory system. Retrieval of stored data through a data transfer system may provide a history of biofeedback readings which could be critical in getting an accurate picture of the physical state of the patient. Potential biofeedback could include transcutaneous bilirubin count, respiration, heart rate, and temperature. Such functionality would probably not be useful for premature infants, since premature infants would normally be confined to a hospital, where biofeedback and data logging capabilities would duplicate or be unnecessary in light of the similar capabilities available in a hospital setting.

This invention can be turned into a commercial product from several different aspects. Because the bodysuit 10 and the base unit 20 are separate pieces, the device may be marketed in two different ways. The bodysuit 10 is designed to be inexpensive to manufacture and disposable, and may be made available in a variety of fabric designs and colors. More than one bodysuit 10 may be made available for purchase for any given patient. Due to the longevity of the base unit 20, it has a potential for reuse that extends beyond the use by one patient. The base unit 20 can easily be "rented out" from a medical supply store, physician's office, or hospital. Two versions of the base unit 20 could be made available for commercial use—a "simple" unit that provides only phototherapy or an advanced unit that provides phototherapy as well as biofeedback and data logging capabilities. The invention may be used for neonates, both term and premature infants, but may also be applied to other phototherapy applications including dermatological applications. If the uses of this product are expanded beyond the neonatal market, the garments, including the bodysuit and base units could be made available for public purchase, allowing for over-the-counter treatment of certain skin disorders.

Figure 5:
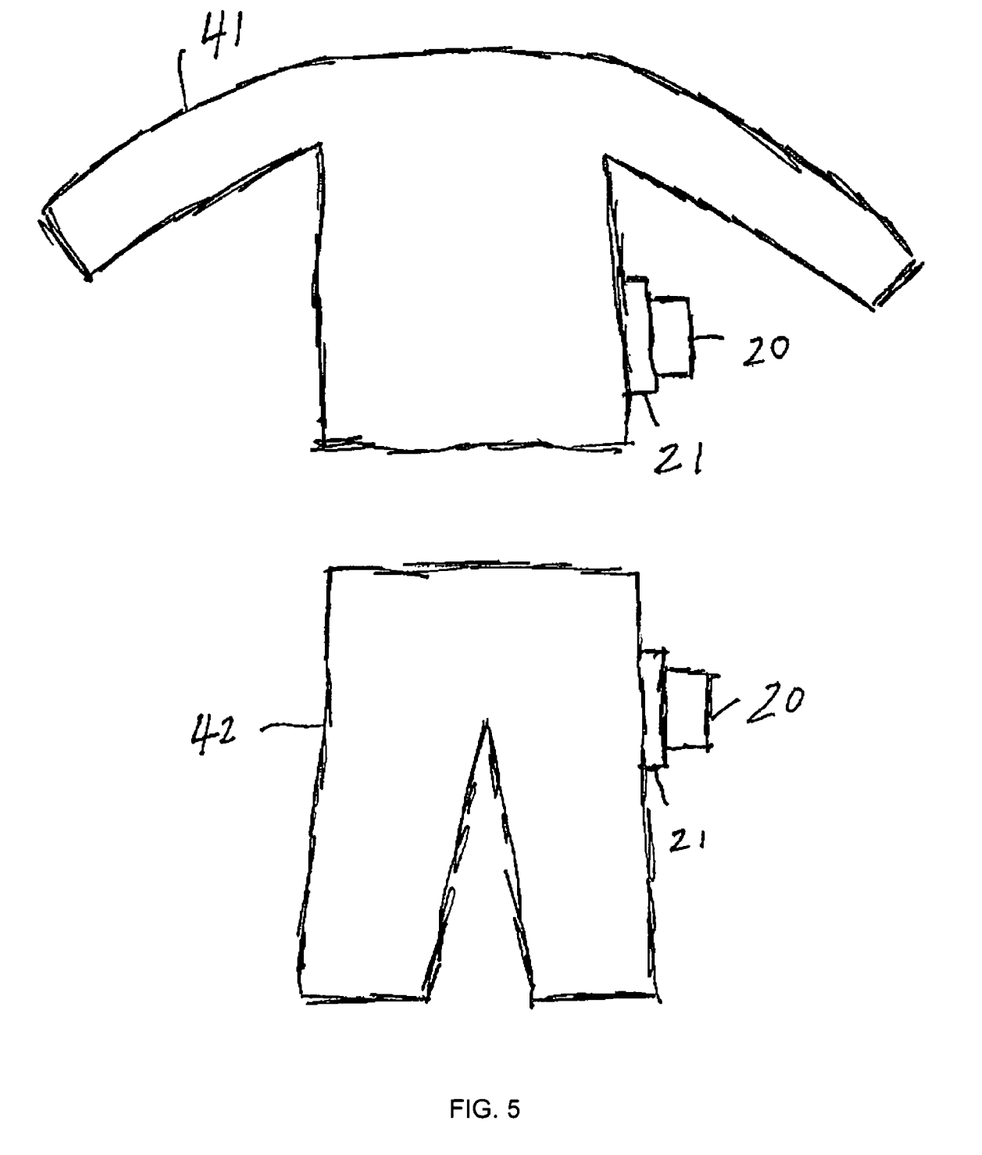
FIG. 5 is a schematic diagram of an alternative embodiment of the present invention in which the bodysuit is in two parts.

In an alternative embodiment as shown in FIG. 5, the bodysuit 10 may be in two pieces, such as a jacket 41 and a pant 42. This is useful when access is needed to one portion of the body of the user while interfering with treatment as little as possible. With the exception of splitting the bodysuit 10 into two pieces 41, 42, the design would be the same as described above for the preferred embodiment with the two pieces 41, 42 operating as separate units, each with its own housing dock 21 and removable base unit 20.

The present invention has been described with reference to certain preferred and alternative embodiments that are intended to be exemplary only and not limiting to the full scope of the present invention as set forth in the appended claims.

What is claimed is:

1. A phototherapy garment for a person, comprising:
 a form-fitting bodysuit adapted to covering substantially all of the arms, legs and torso of the person,
 said form-fitting bodysuit comprising
  a shell of stretchable, washable material, and
  a cross-woven optical fiber layer comprising at least one side-glow optical fiber disposed within said shell, said optical fiber adapted to transmitting at least one wavelength of light at a wavelength and intensity sufficient to provide a therapeutic effect;
 a housing dock affixed to said form-fitting bodysuit and operatively connected to said at least one optical fiber; and
 a base unit removably attachable to said housing dock, said base unit comprising
  at least one light emitting diode generating said light and operatively disposed for transmitting said light to said at least one optical fiber, and
  a power supply operatively connected to said at least one light emitting diode.

2. The phototherapy garment of claim 1, further comprising means for adjustably adapted to fastening said form-fitting bodysuit about the person.

3. The phototherapy garment of claim 1, wherein said base unit is waterproof.

4. The phototherapy garment of claim 1, further comprising three optical fibers operatively connected to three light emitting diodes.

5. The phototherapy garment of claim 4, wherein said three light emitting diodes emit light at wavelengths of 450 nm, 480 nm, and 510 nm, respectively.

6. The phototherapy garment of claim 1, further comprising biofeedback means.

7. The phototherapy garment of claim 1, further comprising data logging means.

8. The phototherapy garment of claim 1, further comprising a reflective layer disposed between said shell and said cross-woven layer of optical fiber.

9. The phototherapy garment of claim 1, further comprising a transparent liner disposed within said cross-woven layer of optical fiber.

10. The phototherapy garment of claim 1, where said power supply comprises a rechargeable battery.

11. The phototherapy garment of claim 1, wherein said bodysuit comprises two parts, a first part adapted to covering at least a portion of the arms, legs and torso of the person and a second part adapted to covering a remaining portion of the arms, legs and torso of the person, and further wherein each of said parts comprises a housing dock and a base unit.

12. The phototherapy garment of claim 1, wherein said bodysuit further comprises open areas adapted to in the armpit and groin area of the body of the person.

13. The phototherapy garment of claim 1, wherein said bodysuit and said housing dock are disposable.

14. The phototherapy garment of claim 10, wherein said base unit comprises an integral electric plug for recharging in a wall outlet.

* * * * *